(12) United States Patent
Chang et al.

(10) Patent No.: US 7,190,450 B2
(45) Date of Patent: Mar. 13, 2007

(54) SYSTEMS AND METHODS FOR SORTING AEROSOLS

(75) Inventors: Richard K. Chang, Hamden, CT (US); Jean-Pierre Wolf, Lyons (FR); Veronique Boutou, Lyons (FR); Yongle Pan, Cheshire, CT (US)

(73) Assignee: Yale University, New Haven, CT (US)

( * ) Notice: Subject to any disclaimer, the term of this patent is extended or adjusted under 35 U.S.C. 154(b) by 464 days.

(21) Appl. No.: 10/766,294

(22) Filed: Jan. 28, 2004

(65) Prior Publication Data

US 2005/0028577 A1 Feb. 10, 2005

Related U.S. Application Data

(60) Provisional application No. 60/506,471, filed on Sep. 26, 2003, provisional application No. 60/448,794, filed on Feb. 20, 2003.

(51) Int. Cl.
*G01J 3/30* (2006.01)

(52) U.S. Cl. ...................................... 356/318

(58) Field of Classification Search .................. None
See application file for complete search history.

(56) References Cited

U.S. PATENT DOCUMENTS

| 4,737,648 | A | * | 4/1988 | Smith et al. | ............ | 250/559.21 |
| 4,756,427 | A | | 7/1988 | Göhde et al. | | |
| 5,561,515 | A | | 10/1996 | Hairston et al. | | |
| 5,730,417 | A | | 3/1998 | Keville et al. | | |
| 5,999,250 | A | * | 12/1999 | Hairston et al. | ............... | 356/73 |
| 6,432,630 | B1 | | 8/2002 | Blankenstein | | |

FOREIGN PATENT DOCUMENTS

DE 40 17 709 12/1991

OTHER PUBLICATIONS

Y. Pan, et al., *Single-shot Florescence Spectra of Individual Micrometer-Sized Bioaerosols illuminated by a 351- or a 266-nm Ultraviolet Laser.* Optics Letters, vol. 24, No. 2, Jan. 15, 1999, pp. 116-118.
R. S. Neve, *Particle Deflection Using Air Jets.* Trans. Inst. M.C., vol. 7, No. 1, Jan.-Mar. 1985, pp. 32-38.
Y. Pan, et al., *Single-Particle Fluorescence Spectrometer for Ambient Aerosols.* Aerosol Science and Technology, vol. 37, 2003, pp. 627-638.

(Continued)

*Primary Examiner*—Tu T. Nguyen
(74) *Attorney, Agent, or Firm*—Ohlandt, Greeley, Ruggiero & Perle, L.L.P.

(57) ABSTRACT

An aerosol deflection system having a concentration zone expelling an air stream through a first detection zone, a second detection zone, and a deflection zone. The first detection zone activates the second detection zone based upon detection of a suspect aerosol of a pre-selected size. The second detection zone activates the deflection zone when the suspect aerosol of the pre-selected size has a predetermined light-induced-fluorescence signature. The deflection zone directs a pressure pulse at the suspect aerosol having the predetermined light-induced-fluorescence signature to deflect the suspect aerosol from the air stream.

20 Claims, 4 Drawing Sheets
(2 of 4 Drawing Sheet(s) Filed in Color)

OTHER PUBLICATIONS

F. L. Reyes, et al., *Bio-Aerosol Fluorescence Sensor*. Field Analytical Chemistry and Technology, vol. 3, 1999, pp. 240-248.

J. D. Eversole, et al., *Continuous Bioaerosol Monitoring Using UV Excitation Fluorescence: Outdoor Test Results*. Field Analytical Chemistry and Technology, vol. 15, 2001, pp. 205-212.

G. A. Luoma, et al., *Real-Time Warning of Biological-Agent Attacks with the Canadian Integrated Biochemical Agent Detection System II (CIBADS II )*. Field Analytical Chemistry and Technology, vol. 3, 1999, pp. 260-273.

Y. Pan, et al., *Characterizing and Monitoring Respiratory Aerosols by Light Scattering*. Optics Letters, vol. 28, No. 8, Apr. 15, 2003, pp. 589-591.

P. Kaye, et al., *Neural-Network-Based Spatial Light-Scattering Instrument for Hazardous Airborne Fiber Detection*. Applied Optics, vol. 36, No. 24, Aug. 20, 1997, pp. 6149-6156.

F. C. Tenover, et al., in *Manual of Clinical Microbiology*. American Society for Microbiology, 1999, pp. 215-235.

J. Ho., *Future of Biological Aerosol Detection*. Analytica Chimica Acta, vol. 457, 2002, pp. 125-148.

P. Belgrader, et al., *PCR Detection of Bacteria in Seven Minutes*. Science, vol. 284, No. 5413, Apr. 16, 1999, pp. 449-450.

S.-I. Makino, et al., *Detection of Anthrax Spores from the Air by Real-time PCR*. Letters in Applied Microbiology, vol. 33, 2001, pp. 237-240.

B. Beatty, et al., *FISH: A Practical Approach*. Oxford University Press, No. 260, 2002, pp. 5-10.

F. Pourahmadi, et al., *Toward a Rapid, Integrated, and Fully Automated DNA Diagnostic Assay for Chlamydia trachomatis and Neisseria gonorrhoeae*. Clinical Chemistry, vol. 46, No. 9, 2000, pp. 1511-1513.

B. K. De, et al., *Two-Component Direct Fluorescent-Antibody Assay for Rapid Identification of Bacillus anthracis*. Emerging Infectious Diseases, vol. 8, No. 10, Oct. 2002, pp. 1060-1065.

C. Hagleitner, et al. *Smart Single-Chip Gas Sensor Microsystem*. Nature, vol. 414, Nov. 15, 2001, pp. 293-296.

T. H. Rider, et al., *A B Cell-Based Sensor for Rapid Identification of Pathogens*. Science, vol. 301, Jul. 11, 2003, pp. 213-215.

M. R. Melamed, et al., *Flow Cytometry and Sorting*, $2^{nd}$. ed., Wiley-Liss, New York, 1990, pp. 1-25.

K. Asano, et al., *The Effect of Particle Velocity on Electrostatic Particle Sorting*. Journal of Electrostatics, vol. 42, 1997, pp. 17-23.

J. R. Bottinger, et al., *An Ink Jet Aerosol Generator*. Journal of Aerosol Science, vol. 29, Supplement 1, pp. S965-S966.

Cheng et al. "Aerosol Science and Technology." http://www.aaar.org/ast_abst/v30n0209.htm.

"Particle Size and Shape with Fluorescense (FL-ASAS)" http://www.biral.com/particle/fluore.htm.

\* cited by examiner

|  Undeflected aerosols (around center) | Deflected aerosols (2 mm from center) |
| --- | --- |
| FIG. 11 — ARD+BG | FIG. 14 — BG |
| FIG. 12 — RBF+BG | FIG. 15 — BG |
| FIG. 13 — NaCl+Tryptophan | FIG. 16 — Tryptophan |

Scale bar: 25 μm

SYSTEMS AND METHODS FOR SORTING AEROSOLS

CROSS REFERENCE TO RELATED APPLICATIONS

This application claims the benefit of U.S. Provisional Application Ser. No. 60/506,471 filed on Sep. 26, 2003 and the benefit of U.S. Provisional Application Ser. No. 60/448,794 filed on Feb. 20, 2003, the contents of each are incorporated by reference herein in their entirety.

BACKGROUND OF THE INVENTION

1. Field of the Invention

The present disclosure is related to aerosol sorting. More particularly, the present disclosure is related to systems and methods for on demand sorting of pathogenic biological aerosols.

2. Description of Related Art

The events of the present day have made real time detection of pathogenic biological aerosols a necessity for both civilian and military applications. For example, recent outbreaks of airborne illnesses, such as Sudden Acute Respiratory Syndrome (SARS), recent terrorist motivated biological attacks, and other events all highlight the need for real time detection and identification of pathogenic biological aerosols. As used herein, the term "aerosol" shall mean any suspension of solid or liquid particles in a gas, such as air. Thus, pathogenic biological aerosols are those airborne viruses or bacteria that cause or are capable of causing disease.

Biochemical techniques exist that can identify genus and species of many biological aerosols. However, these techniques often take a long time to obtain results. Moreover, the results of these techniques are often hampered by background or ambient aerosols and, thus, detecting pathogenic biological aerosols in the wide-variety of background aerosols (usually fewer than 1 in $10^5$) is analogous to looking for a needle in the haystack.

Accordingly, it has been determined by the present application that there is a need for systems and methods that sort pathogenic aerosols from ambient air samples.

SUMMARY OF THE INVENTION

Systems and methods for sorting biological aerosols from ambient air in real time are provided.

The present disclosure provides systems and methods for discriminating between pathogenic and non-pathogenic biological aerosols such that the pathogens can be sorted from ambient air in real time.

The present disclosure also provides a compact and/or portable system and method for pathogenic biological aerosol sorting.

The present disclosure also provides an efficient biological aerosol sorter having an aerodynamic deflector cued by fluorescence from the biological aerosols.

The present disclosure also provides systems and methods for sorting pathogenic biological aerosols from ambient air with an enrichment factor of at least about $6 \times 10^6$.

In one embodiment, an aerosol sorting system is provided. The system has a concentration zone configured to expel an air stream through a first detection zone, a second detection zone, and a deflection zone. The first detection zone activates the second detection zone based upon detection of a suspect aerosol of a pre-selected size. The second detection zone activates the deflection zone when the suspect aerosol of the pre-selected size has a predetermined signature. The deflection zone directs a pressure pulse at the suspect aerosol having the predetermined signature to deflect the suspect aerosol from the air stream.

A method for sorting aerosols from ambient air is also provided. The method includes generating a defined stream of the ambient air; causing a suspected aerosol in the defined stream to emit a signature when the suspect aerosol has a predetermined size; detecting the signature from the suspected aerosol; and removing the suspected aerosol from the defined stream with a pressure pulse when the signature is determined to be a predetermined signature.

The above-described and other features and advantages of the present disclosure will be appreciated and understood by those skilled in the art from the following detailed description, drawings, and appended claims.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
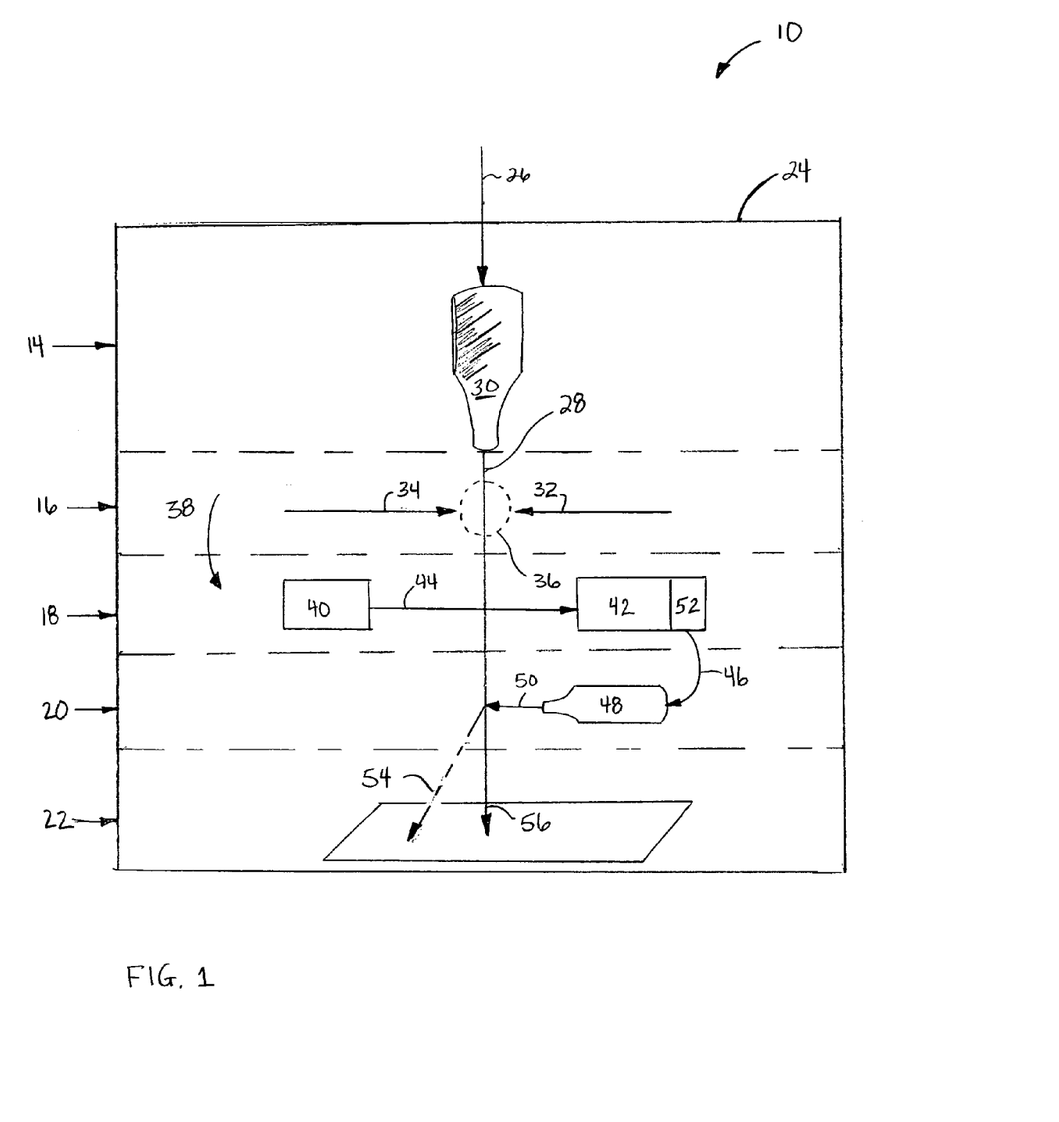
FIG. 1 is a side schematic view of an exemplary embodiment of a real time aerosol sorting system according to the present disclosure.

Referring now to the figures, and in particular to FIG. 1, an exemplary embodiment of a system 10 capable of real time sorting of pathogenic biological aerosols from an air sample is illustrated. System 10 is configured to rapidly sort aerosols having a diameter of less than about 10 micrometers (μm) from a stream of ambient air, or other gas stream as needed, based on a combination of aerosol size data and fluorescence spectrum of the aerosol. Thus, system 10 is configured to rapidly classify the aerosols in the air stream based on several measured parameters. Advantageously, system 10 is compact and/or portable, which allows the system to be used discretely in a site to be sampled, such as an airport or hospital, and allows the system to be easily moved through out the area.

System 10 has at least one detection zone and at least one deflection zone. In the exemplary embodiment illustrated by FIG. 1, system 10 has a concentration zone 14, a first detection zone 16, a second detection zone 18, and a deflection zone 20. In some embodiments, system 10 can includes a collection zone 22. System 10 can also include housing 24 for enclosing one or more of zones 14–22. Preferably, housing 24 encloses all of the zones of system 10.

Concentration zone 14 is configured to draw ambient air 26 into system 10 and expel the air in a stream 28. For example, concentration zone 14 can include an aerodynamic focusing nozzle 30 that expels defined stream 28 in a first direction, which is projected through zones 16–20. Stream 28 is, preferably, a laminar air stream having a diameter of about 600 micrometers (μm) and a speed of about 10 meters per second (m/s). Of course, it is contemplated by the present disclosure for stream 28 to have a larger or smaller diameter and/or speed, as well as for the stream to have laminar portions and non-laminar portions.

First detection zone 16 can be configured to detect the size of the aerosols in stream 28. In a preferred embodiment, first detection zone 16 uses Doppler velocimetry (LDV) also known as laser Doppler anemometry. Here, two coherent laser beams 32, 34 with different angles of incidence and different wavelengths are focused on a sample volume 36 of stream 28. The aerosols in stream 28 simultaneously scatter light from laser beams 32, 34. One or more photo-detectors (not shown) receive the scattered light and generate a frequency representing the heterodyne difference in Doppler shift frequencies produced by aerosol motion relative to the beams. The elastic scattering signals from laser beams 32, 34 as received by the photo-detector(s) can be used to determine size and speed of the aerosols in sample volume 36.

An example LDV system is disclosed in U.S. Pat. No. 5,561,515 to Hairston et al. the contents of which are incorporated by reference herein. Of course, it should be recognized that other means for detecting the size of the aerosols in stream 28 are contemplated by the present disclosure.

First detection zone 16 activates second detection zone 18 upon detection of a suspect aerosol of a pre-selected size in sample volume 36. For example, when the elastic scattering signals from laser beams 32, 34 as received by the photo-detector(s) are in a predetermined voltage range (corresponding to a pre-selected aerosol size), first detection zone 16 provides a first signal 38 to activate second detection zone 18.

Figure 2:
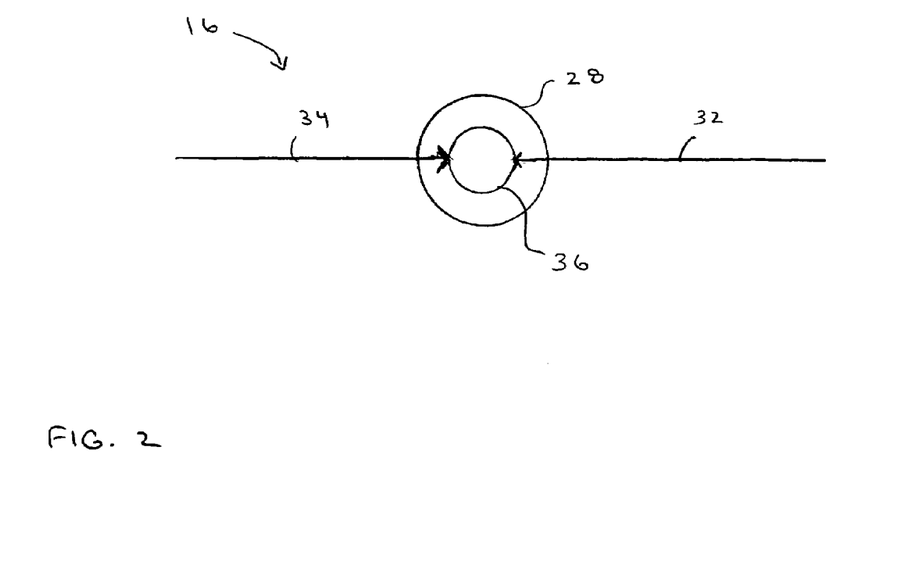
FIG. 2 is a top view of a first detection zone of the system of FIG. 1.

In one embodiment of the present disclosure, sample volume 36 has a diameter that is smaller than the diameter of stream 28 as seen in FIG. 2. For example, stream 28 can have a diameter of about 600 μm and sample volume 36 can have a diameter of about 300 μm. Since sample volume 36 is smaller than stream 28, any aerosols outside of the sample volume but in the stream are not detected by first detection zone 16. Here, aerosols outside of sample volume 36 but in stream 28 do not cause first detection zone 16 to activate second detection zone 18. Of course, it is contemplated by the present disclosure for system 10 to have a sample volume 36 with a diameter that is at least equal to the diameter of the stream 28. Alternately, it is contemplated by the present disclosure for system 10 to have more than one sample volume 36 providing larger sample coverage of the diameter of the stream 28 than possible with one sample volume.

Second detection zone 18 has an excitation source 40 and a detector 42. In one embodiment, second detection zone 18 uses light-induced-fluorescence (LIF). Here, excitation source 40 is a light source such as can be a laser, a light emitting diode, a lamp, and any combinations thereof and detector 42 is a spectrally resolved photo-detector such as a spectrometer, spectral filters with a photodiode, a photomultiplier tube (PMT), a photodiode array, and any combinations thereof.

Second detection zone 18 performs a spectral analysis of the fluorescence of aerosols in stream 28 upon receipt of first signal 38. Advantageously, second detection zone 18 can distinguish between biological and non-biological aerosols since light-induced-fluorescence from biological aerosols have a particular fluorescence spectral finger signature. Further, system 10 can use the spectral signatures of the biological aerosols to determine if the aerosols are pathogenic or non-pathogenic. In some embodiments, system 10 can be calibrated such that the light-induced-fluorescence signature can determine if the biological aerosol is alive or dead.

Second detection zone 18 can be triggered within about 3 microseconds (μs) from the time a suspect aerosol is detected by first detection zone 16. Second detection zone 18 is positioned with respect to first detection zone 16 to account for this trigger time. In the example where the speed of the stream is about 10 m/s, suspect aerosols detected by first detection zone 16 travel about 30 μm during the 3 μs trigger time. Here, light source 40 and spectrally resolved photo-detector 42 can be positioned about 30 μm below sample volume 36.

Light source 40 radiates light 44 through stream 28. Light 44 can be monochromatic light, multi-spectral light, ultraviolet light, broad spectrum light, and any combinations thereof. Once activated, light 44 from light source 40 excites the biological aerosols in stream 28 to a higher energy state, causing the aerosols to emit light-induced-fluorescence from the UV to the visible. Spectrally resolved photo-detector 42 detects the light-induced-fluorescence (LIF) from the biological aerosols in stream 28. Second detection zone 18 compares the light-induced-fluorescence signature for the aerosols in stream 28 as detected by spectrally resolved photo-detector 42 to predetermined LIF signatures for one or more suspect biological aerosols. Based on this comparison, second detection zone 18 generates a second signal 46 when suspect biological aerosols are detected, where the second signal 46 is configured to activate sorting zone 20.

Since system 10 generates second signal 46 based on the whole fluorescence spectrum as detected by second detection zone 18, the system is capable of distinguishing aerosols with similar fluorescence peaks, which would otherwise not be determinable using only two fluorescence bands divided by ultraviolet or visible range.

In some embodiments of the present disclosure, the elastic scattering pattern from laser beams 32, 34 can be used along with or in the absence of the LIF signature to generate second signal 46.

It should be recognized that second detection zone 18 is described above by way of example making use of LIF. Of course, it is contemplated by the present disclosure for second detection zone 18 to use Laser Induced Breakdown Spectroscopy (LIBS) instead of fluorescence. Here, second detection zone 18 detects plasma generation information about the aerosol composition.

Advantageously, system 10 is configured to deflect the suspect aerosol into suspect portion 54 on demand. Specifically, second detection zone 18 is configured to rapidly generate second signal 46 and is positioned with respect to deflection zone 20 to account for the rapid generation time. For example, in one embodiment of the present disclosure second detection zone 18 is configured to generate second signal 46 in less than about 20 μs, more preferably less than about 14 μs, with less than about 8.7 μs being most preferred. In the example where the speed of stream 28 is about 10 m/s and the generation time is 20 μs, suspect aerosols detected by second detection zone 18 travel about 200 μm. Here, second detection zone 18 can be positioned about 200 μm from light source 40.

In one embodiment of second detection zone 18 according to the present disclosure, spectrally resolved photo-detector 42 is based on a multi-channel PMT having at least two channels, more preferably at least sixteen channels, with at least thirty-two channels being most preferred. Here, second detection zone 18 includes an integrated comparison circuit 52 in parallel communication with PMT 42. Circuit 52 has resident thereon the predetermined LIF signatures for one or more suspect biological aerosols. Circuit 52 compares the light-induced-fluorescence signature detected by PMT 42 to the predetermined LIF signatures resident on the circuit and generates second signal 46 when suspect biological aerosols are detected. In this manner, second detection zone 18 mitigates the need for an external processor to perform the required comparison operation and signal generation operation. Thus, second detection zone 18 rapidly generates second signal 46, which allows system 10 to deflect suspect aerosols into suspect portion 54 in real time (i.e., on demand).

Deflection zone 20 has a deflection device 48 configured selectively to emit a pressure pulse 50 towards stream 28 upon receipt of second signal 46 from second detection zone 18. Pressure pulse 50 is sufficient to deflect aerosols from stream 28. Thus, pressure pulse 50 deflects stream 28 into a suspect portion 54 and a non-suspect portion 56.

In one exemplary embodiment, stream 28 has a substantially vertical (i.e., downward) direction and pressure pulse 50 has a substantially horizontal direction. Of course, it is contemplated by the present disclosure for stream 28 and/or pressure pulse 50 to have any desired direction, where the pressure pulse can impinge on the stream.

Advantageously, deflection zone 20 enables system 10 to be more compact and/or portable, less destructive to the deflected aerosols, and more independent of the condition of ambient air 26 than previously possible. Devices that electrostatically sort aerosols suspended in a flowing fluid, such as flow cytometry devices, are known. Here, aerosols to be sorted are suspended in a fluid, charged to a known electrical state, and then subsequently deflected based on that electrical state. Thus, electrostatic sorting devices require both a charging device and a deflecting device, which are larger than the simple deflection device 48 of system 10. Consequently, system 10 can be substantially smaller and more compact as compared to electrostatic deflection devices.

It has also been determined that deflection device 48 is less destructive than electrostatic deflection as it does not change the electrical state of the aerosols. Thus, it has been determined that system 10 mitigates damage to the deflected aerosols in stream 28. Further, it has been found that deflection device 48 is more robust to changing conditions in ambient air 26. For example, the electrical state used in electrostatic deflection can be dependent on various physical properties of the aerosols, as well as the properties of ambient air 26, such as humidity and temperature.

Figure 3:
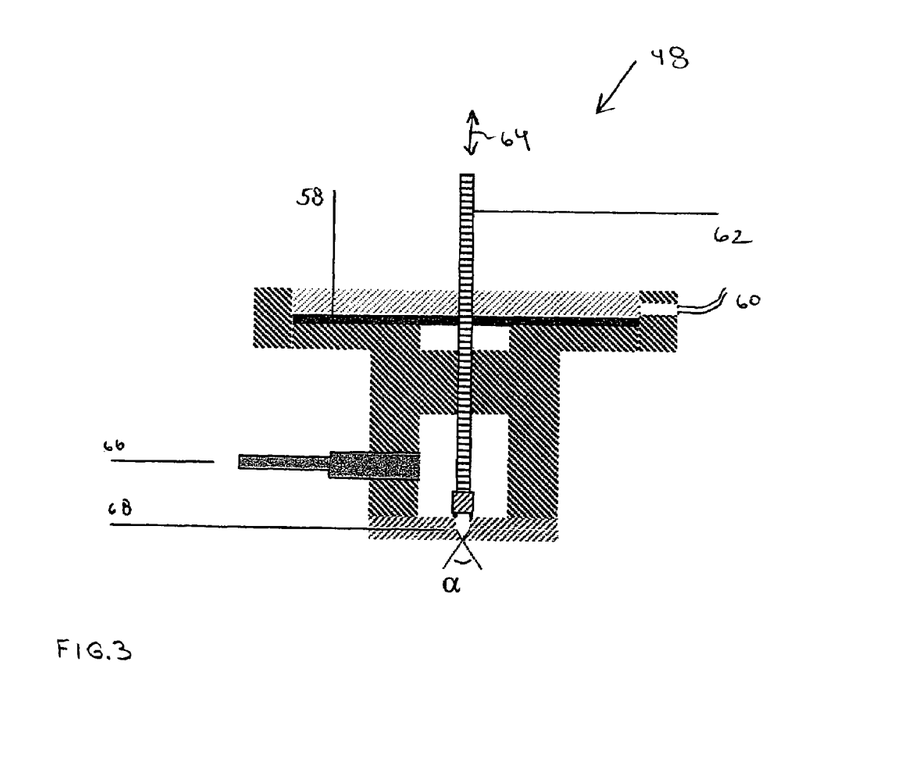
FIG. 3 is a cross sectional view of an exemplary embodiment of a deflection device according to the present disclosure.

Advantageously, system 10 also configured to mitigate deflection of surrounding non-suspect aerosols into suspect portion 54. For example, system 10 rapidly cycles a tightly focus pressure pulse to deflect as few aerosols as possible from stream 28. Referring now to FIG. 3, an exemplary embodiment of deflection device 48 having a rapid cycle time is illustrated. Here, deflection device 48 is a piezoelectric pulsed valve having a piezoelectric disk 58 in electrical communication with a power supply 60. Disk 58 is configured to move a valve rod 62 along direction 64 in response to the application of power from power supply 60. In an exemplary embodiment, disk 58 has a diameter of about 2 inches.

Deflection device 48 also has a pressure source 66 feeding a nozzle 68. Rod 62 has a first position closing nozzle 68 such that pressure source 66 is not in fluid communication with the nozzle, preventing deflection device 48 from emitting pressure pulse 50. Rod 62 also has a second position (not shown) such that pressure source 66 is in fluid communication with the nozzle, causing deflection device 48 to emit pressure pulse 50. In this manner, deflection device 48 is configured to emit pressure pulse 50 having about 18 pounds per square inch (psi), which has been found to be sufficient to deflect stream 28 into suspect portion 54 and non-suspect portion 56.

Deflection device 48 is configured to focus pressure pulse 50 to diameter of about 500 µm, which allows the pressure pulse to propagate several millimeters from the nozzle. In addition, deflection device 48 emits pressure pulse 50 for a very short duration of about 60 µs (microseconds). Thus, pressure pulse 50 is well-localized and causes a very short interruption in stream 28, which ensures that as few aerosols proximate to the suspected aerosol are deflected from the stream 28. Specifically, pressure pulse 50 is configured to deflect suspect portion 54 from stream 28 equal to: $\square R^2 v(t)$, where R is the radius of stream 28, v is the velocity of the stream, and t is the duration of pressure pulse 50.

For example, assume that stream 28 has one suspect aerosol entrained in 100,000 aerosols per liter, a radius of 300 µm, and a velocity of 10 m/s. Also, assume that pressure pulse 50 has a duration of 60 µs. Therefore, suspect portion 54 has a volume of about $1.7 \times 10^{-7}$ liters, which correlates to about $1.7 \times 10^{-2}$ aerosols. After this procedure one biological aerosol is detected within $1.7 \times 10^{-2}$ aerosol particles which is to be compared to the initial concentration of one biological aerosol in 100,000. The enrichment factor is therefore $100,000/1.7 \times 10^{-2} = 6 \times 10^6$.

In addition, deflection device 48 has a response time of less than about 20 µs from the time that it receives second signal 46. Because the suspect aerosols do not need to pass through a charging area with a long delay, and the response time of deflection device 48 is less than 20 µs, system 10 is configured to precisely deflect a suspect aerosol within 200 µm (micrometers) from the time when second detection zone 18 provides second signal 46. Again, system 10 can be substantially smaller and more compact as compared to electrostatic deflection devices.

In one embodiment, second detection zone 18 generates second signal 46 in less than about 20 µs from the time when the suspected aerosol is excited by light 44, deflection zone 20 begins deflecting the suspected aerosol in less than about 20 µs from receipt of the second signal, and completes the deflection in about 60 µs. Accordingly, system 10 radiates and deflects suspected aerosols from steam 28 in less than about 100 µs. The compact nature of system 10 results from this rapid response time. Further, system 10 provides the desired enrichment factor as a result of this rapid response time.

Further, deflection device 48 is configured to cycle from open, to closed, to open in about 60 µs. Thus, deflection zone 20 can selectively deflect aerosols that are about 500 µm apart from one another since stream 28 has a velocity of 10 m/s.

It should be recognized that system 10 is described above by way of example deflecting the suspect aerosols from stream 28 using one positive pressure deflection device 48 to push the suspect aerosol from the stream. Of course, it is contemplated by the present disclosure for system 10 have more than one deflection device 48. It is also contemplated by the present disclosure for system 10 to deflect non-suspect aerosols from stream 28, thus leaving any suspect aerosols in the stream for further processing. It is also contemplated by the present disclosure for system 10 to deflect aerosols (suspect or non-suspect) from stream 28 using a negative pressure pulse to pull the suspect aerosol from the stream. Further, it is contemplated by the present disclosure for system 10 to deflect aerosols from stream 28 using a combination of negative and positive pressure to push and pull the various aerosols in desired directions. Moreover, it is contemplated by the present disclosure for system 10 to modify the deflection force and/or deflection direction based the type of aerosol detected. Here, system 10 can deflect a first type of aerosol to a first location, but a second type of aerosol to a second location.

Accordingly, deflection zone 20 is configured to deflect suspect portion 54 from non-suspect portion 56. In one embodiment, collection zone 22 collects suspect portion 54 for further analysis and/or pathogen identification. Here, the enrichment of stream 28 by the aforementioned enrichment factor serves to make further analysis and/or pathogen identification of suspect portion 54 easier, more reliable, and/or faster than possible when using only ambient air 26. For example, collection zone 16 can include one or more devices (not shown) providing for further analysis and/or pathogen identification using methods, such as, but not limited to, biochemical assays, spectroscopic techniques (Raman or FTIR), and others. If using only ambient air 26, the large quantity of background aerosols could contaminate the reactions, disable the biochemical assays, mask the Raman and IR peaks, and other deleterious effects. In contrast, use of enriched suspect portion 54 mitigates one or more of the aforementioned deleterious effects.

In other embodiments, collection zone 22 collects both suspect portion 54 and non-suspect portion 56. In still other embodiments, collection zone 22 collects only non-suspect portion 56 and, thus, system 10 acts to filter the suspect aerosols from ambient air 26.

Experimental Results—Test #1

A mixture having about 85% of non-suspect aerosols and about 15% of suspect biological aerosols was used to test system 10. Tryptophan aerosols were used as suspect biological aerosols, while riboflavin (RBF) was used as the background or non-suspect aerosols. The aerosols of tryptophan and RBF were obtained using ink-jet aerosol generators and mixed to flow into the aerosol stream. The results of this first test are illustrated in FIGS. 4 through 10. Collection zone 22 included a microscope glass slide positioned one centimeter (cm) beneath nozzle 30 for collecting suspect portion 54 in a first area 70 and non-suspect portion 56 in a second area 72. A fluorescence microscope (Olympus BX60) and a color digital camera (Diagnostic Instruments Inc. 2.2.0) were used to image the collected aerosols when illuminated by a UV light source and a weak background white light such that tryptophan exhibits a blue color with a round shape, while RBF exhibits a yellow color with a needle-like crystalline shape.

Figure 4:
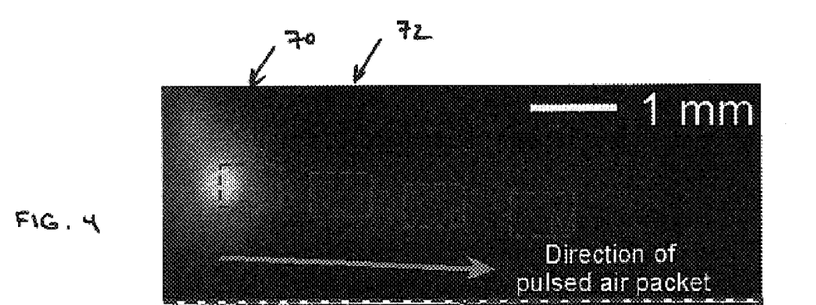
FIGS. 4 through 10 are color photographs illustrating first experimental results of the real time aerosol sorting system of FIG. 1.
Figure 5:
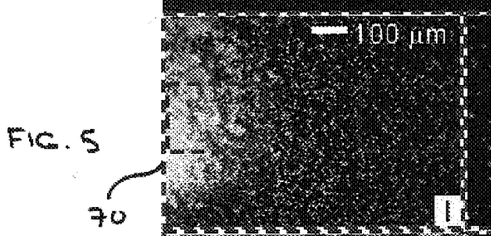
Figures 6, 7:
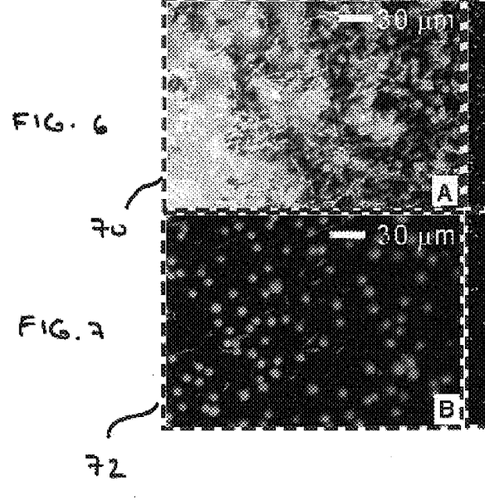
Figure 8:
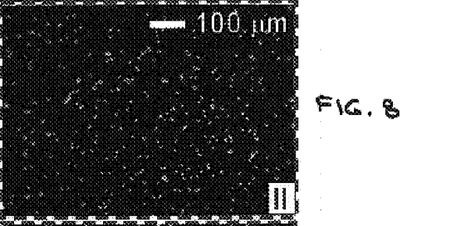
Figure 9:
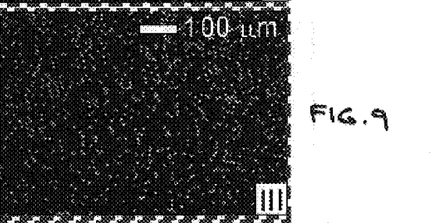
Figure 10:
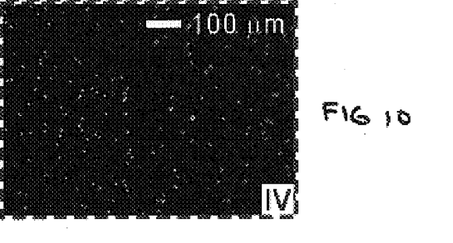

FIG. 4 illustrates the entire collection zone 22, which includes both first and second areas 70, 72. FIGS. 5 through 7 illustrate, at increasing magnification levels, the aerosols collected in first area 70, while FIGS. 8 through 10 illustrate, at increasing magnification levels, the aerosols collected in second area 72. As can be seen, most of the aerosols remaining in first area 70 are RBF aerosols, namely non-suspect portion 56. However, the tryptophan aerosols (i.e., suspect portion 54) are primarily located in second area 72, which is defined along the direction of pressure pulse 50.

As seen in FIG. 9, the highest density of tryptophan aerosols in second area 72 is found at about 2 millimeters (mm) from the center of the RBF aerosols in first area 70. Only a few RBF aerosols are deflected 1 mm away from the center and substantially none beyond the 1 mm distance. By counting the concentration ratio of tryptophan to RBF aerosols in second area 72 beyond 1 mm, the result shows that the enriching factor is higher than $10^4$ in this test In the tested embodiment of system 10, sample volume 36 has a smaller diameter (i.e., 300 μm) than the diameter of stream 28 (i.e., 600 μm). Thus, any aerosols outside of sample volume 36 but in stream 28 were not detected by first detection zone 16. This creates a high density of undeflected tryptophan aerosols around the central RBF aerosols in first area 70 as best seen at the right side of FIG. 5, about 400 μm from the center of the first area.

Experimental Results—Test #2

A second mixture having about 85% of non-suspect aerosols and about 15% of suspect biological aerosols was also used to test system 10. In this test, *Bacillus subtilis* ("BG") or tryptophan aerosols were used as suspect biological aerosols, where BG is used to simulate anthrax. Arizona road dust (ARD), riboflavin (RBF), or sodium chlorine (NaCl) were used as background or non-suspect aerosols. ARD is one of the standard background aerosols. RBF is a biological material but has a shape and fluorescence spectrum different from BG aerosols. NaCl has a shape similar to the suspect aerosols. The mixed aerosols from one of the suspect aerosols and one of the background aerosols were obtained by combining the outputs of two ink-jet aerosol generators.

The results of this second test are illustrated in FIGS. 11 through 16. Here, the fluorescent aerosols (e.g., BG, RBF, and tryptophan) are observed by their fluorescence images induced by UV lamp illumination, while ARD and NaCl aerosols are observed with an additional white light illumination.

Figure 11:
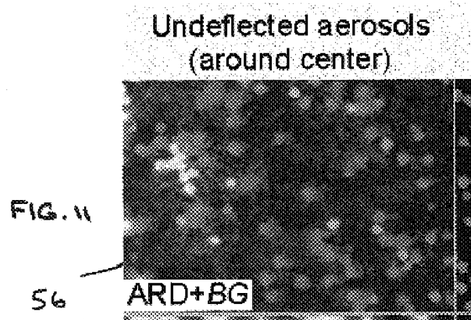
FIGS. 11 through 16 are color photographs illustrating second experimental results of the real time aerosol sorting system of FIG. 1.
Figure 12:
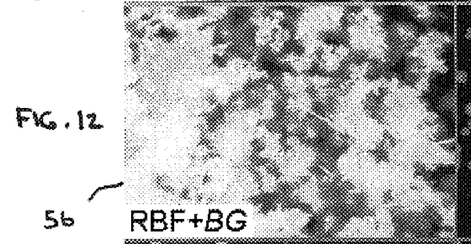
Figure 13:
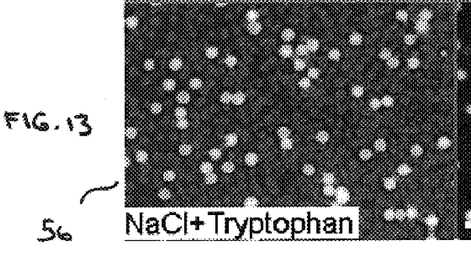
Figure 14:
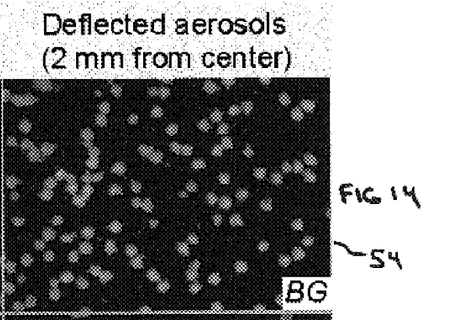
Figure 15:
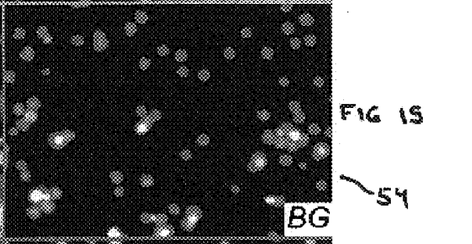
Figure 16:
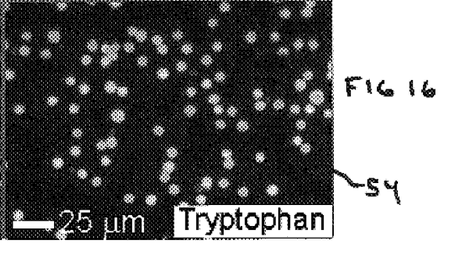

FIGS. 11 through 13 illustrate that the center of non-suspect portion 56 is dominated by ARD, RBF, or NaCl aerosols. Conversely, FIGS. 14 through 16 illustrate that 2 mm from the center of non-suspect portion 56 along the direction of the pressure pulse is mainly occupied by the suspect portion 54 of BG or tryptophan. Accordingly, system 10 sorts suspect aerosols based on their similar LIF fingerprint, despite background aerosol fluorescence or aerosols similarly shaped to the BG aerosols. The counting results show that all enrichment factors are higher than $10^4$.

Accordingly and as set forth herein, system 10 combines rapid aerodynamic or pressure based sorting with two or more rapid detection zones to provide selective and efficient sorting of potentially pathogenic biological aerosols from background aerosols. System 10 can also be used to deflect aerosols depending on properties other than fluorescence, such as aerosol size, morphology from elastic scattering patterns, and any combinations thereof.

It should be noted that the terms "first", "second", "third", "upper", "lower", and the like may be used herein to modify various elements. These modifiers do not imply a spatial, sequential, or hierarchical order to the modified elements unless specifically stated. It should also be noted that the ranges provided herein, if any, are meant to include all subranges therebetween unless specifically stated to the contrary.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. An aerosol deflection system comprising:
a concentration zone configured to expel an air stream through a first detection zone a second detection zone, and a deflection zone;
said first detection zone configured to activate said second detection zone based upon detection of a suspect aerosol of a pre-setected size;
said second detection zone configured to activate said deflection zone when said suspect aerosol of said pre-selected size has a predetermined signature; and
said deflection zone configured to direct a pressure pulse at said suspect aerosol having said predetermined signature to deflect the suspect aerosol from said air stream.

2. The system of claim 1, wherein said suspect aerosol is a pathogenic biological aerosol.

3. The system of claim 2, wherein the system deflects said suspect aerosol from ambient air with an enrichment factor about $6 \times 10^6$.

4. The system of claim 1, further comprising a collection zone configured to collect said suspect aerosols deflected by said deflection zone, said collection zone comprising one or more pathogen identification devices configured to further analyze said suspect aerosols deflected by said deflection zone.

5. The system of claim 1, wherein said predetermined signature is a predetermined LIBS signature.

6. The system of claim 1, wherein said predetermined signature is a predetermined LIF signature.

7. The system of claim 6, wherein said second detection zone comprises:
a light source configured to radiate light at said suspect aerosol of said preselected size; and
a spectrally resolved photo-detector configured to detect a resultant LIF signature.

8. The system of claim 7, further comprising an integrated circuit in parallel communication with said spectrally resolved photo-detector, said integrated circuit having said predetermined LIF signatures resident thereon for comparison with said resultant LIF signature.

9. The system of claim 7, wherein said spectrally resolved photo-detector comprises at least two channels.

10. The system of claim 7, wherein said spectrally resolved photo-detector comprises at least thirty-two channels.

11. The system of claim 1, wherein said pressure pulse is selected from the group consisting of a positive pressure pulse, a negative pressure pulse, and any combination of the foregoing.

12. The system of claim 1, wherein said first detection zone is further configured to activate said second detection zone based upon elastic scattering signals.

13. A method for deflecting aerosols from ambient air using the system of claim 1, comprising:
generating said air stream of the ambient air;
causing said suspect aerosol suspended in said air stream to emit a signature when said suspect aerosol has said predetermined size;
detecting said signature from said suspect aerosol; and
removing said suspected aerosol from said air stream via said pressure pulse when said signature is said predetermined signature.

14. The method of claim 13, further comprising removing said suspect aerosol from said defined stream in less than about 100 microseconds from the time said suspect aerosol is caused to emit said signature.

15. The method of claim 13, wherein suspected aerosols are removed from said air stream with an enrichment factor of about $6 \times 10^6$.

16. The method of claim 13, further comprising analyzing said suspect aerosol after removing it from said air stream.

17. The method of claim 13, wherein said pressure pulse is selected from the group consisting of a positive pressure pulse, a negative pressure pulse, and any combination of the foregoing.

18. The method of claim 13, further comprising receiving elastically scattered signals from at least two laser beams to determine said predetermined size.

19. The method of claim 18, wherein removing said suspected aerosol is further based on said elastically scattered signals.

20. The method of claim 13, wherein said signature is a LIBS signature or a LIF signature.

* * * * *